US011479771B2

(12) United States Patent
Van Diepen et al.

(10) Patent No.: US 11,479,771 B2
(45) Date of Patent: *Oct. 25, 2022

(54) ANTISENSE OLIGONUCLEOTIDES FOR THE TREATMENT OF EYE DISEASE

(71) Applicant: ProQR Therapeutics II B.V., Leiden (NL)

(72) Inventors: Hester Catharina Van Diepen, Leiden (NL); Janne Juha Turunen, Leiden (NL); Hee Lam Chan, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 202 days.

This patent is subject to a terminal disclaimer.

(21) Appl. No.: 16/784,410

(22) Filed: Feb. 7, 2020

(65) Prior Publication Data

US 2020/0181616 A1 Jun. 11, 2020

Related U.S. Application Data

(63) Continuation of application No. 16/336,069, filed as application No. PCT/EP2017/074133 on Sep. 22, 2017, now Pat. No. 10,612,025.

(30) Foreign Application Priority Data

Sep. 23, 2016 (GB) .................................. 1616202

(51) Int. Cl.
*C12N 15/113* (2010.01)
*A61K 31/7088* (2006.01)
*A61K 31/712* (2006.01)

(52) U.S. Cl.
CPC ........ *C12N 15/113* (2013.01); *A61K 31/7088* (2013.01); *A61K 31/712* (2013.01); *C12N 2310/11* (2013.01); *C12N 2310/321* (2013.01)

(58) Field of Classification Search
None
See application file for complete search history.

(56) References Cited

U.S. PATENT DOCUMENTS

| 7,250,496 B2 | 7/2007 | Bentwich |
| 10,612,025 B2 | 4/2020 | Van Diepen |

FOREIGN PATENT DOCUMENTS

| EP | 1619249 | 9/2008 |
| EP | 2425814 | 3/2012 |
| WO | WO 2012151324 | 11/2012 |
| WO | WO 2015134812 | 9/2015 |
| WO | WO 2016005514 | 1/2016 |

OTHER PUBLICATIONS

Bainbridge et al, "Effect of gene therapy on visual function in Leber's congenital amaurosis," N. Engl. J. Med., 2008, 358:2231-2239.
Cirak et al, "Exon skipping and dystrophin restoration in patients with Duchenne muscular dystrophy after systemic phosphorodiamidate morpholino oligomer treatment: an open-label, phase 2, dose-escalation study," Lancet, 2011, 378(9791 ):595-605.
Cirak et al, "Restoration of the Dystrophin-associated Glycoprotein Complex after Exon Skipping Therapy in Duchenne Muscular Dystrophy," Mol. Ther., 2012, 20:462-467.
Dorn and Kippenberger, "Clinical application of CpG-, non-CpG-, and antisense oligodeoxynucleotides as immunomodulators," Curr. Opin. Mol. Ther., 2008, 10(1):10-20.
Egholm et al, "Conformationally Constrained (Coumarin-Triazolyl-Bipyridyl) Click Fluoroionophore as a Selective Al3+ Sensor," Nature, 1993, 365:566-568.
Goemans et al, "Systemic administration of PRO051 in Duchenne's muscular dystrophy," N. Engl. J. Med., 2011, 364(16):1513-1522).
Gorman et al, "Stable alteration of pre-mRNA splicing patterns by modified U7 small nuclear RNAs," Proc. Natl. Acad. Sci. USA, 1998, 95(9):4929-34.
Govindaraju & Kumar, "Backbone-extended pyrrolidine peptide nucleic acids (bepPNA): design, synthesis and DNA/RNA binding studies," Chem. Commun., 2005, pp. 495-497.
Hartong et al, "Retinitis pigmentosa," Lancet, 2006, 368(9549): 1795-1809.
Hashimoto et al, "Lentiviral gene replacement therapy of retinas in a mouse model for Usher syndrome type 1 B," Gene. Ther., 2007, 14(7):584-594.
Kimberling et al, "Frequency of Usher syndrome in two pediatric populations: implications for genetic screening of deaf and hard of hearing children," Genet. Med., 2010 12:512-516.
Lenassi et al, "The effect of the common c.2299delG mutation in USH2A on RNA splicing," Exp Eye Res, 2014, 122:9-12.
McGee et al, "Novel mutations in the long isoform of the USH2A gene 25 in patients with Usher syndrome type II or non-syndromic retinitis pigmentosa," J Med Genet, 2010, 47(7):499-506.
Morita et al, "2'-O, 4'-C-Ethylene-bridged nucleic acids (ENA) with nuclease-resistance and high affinity for RNA," Nucleic Acid Res Supplement, 2001, 1:241-242.
Nielsen et al, "Sequence-Selective Recognition ofDNA by Strand Displacement with a Thymine-Substituted Polyamide," Science, 1991, 254:1497-1500.
Okita, et al., "A more efficient method to generate integration-free human iPS cells," Nat. Methods, 2011, 8:409-412.
PCT International International Preliminary Report on Patentability, No. PCT/EP2017/074133, dated Apr. 4, 2019, 8 pages.
PCT International Search Report and Written Opinion in International Appln. No. PCT/EP2017/074133, dated Aug. 12, 2017, 12 pages.
Sangermano, et al., "Photoreceptor Progenitor mRNA Analysis Reveals Exon Skipping Resulting from the ABCA4 c.5461-10T→C Mutation in Stargardt Disease," Ophthalmology, 2016, 123(6):1375-85.
Scaffidi and Misteli, "Reversal of the cellular phenotype in the premature aging disease Hutchinson-Gilford progeria syndrome," Nat. Med., 2005, 11(4):440-445.
Suter et al, "Double-target antisense U7 snRNAs promote efficient skipping of an aberrant exon in three human beta thalassemic mutations," Hum. Mol. Genet., 1999, 8(13):2415-23.

(Continued)

*Primary Examiner* — Tracy Vivlemore
(74) *Attorney, Agent, or Firm* — Fish & Richardson P.C.

(57) ABSTRACT

The invention relates to the fields of medicine and immunology. In particular, it relates to novel antisense oligonucleotides (AONs) that may be used in the treatment, prevention and/or delay of Usher syndrome type II and/or USH2A-associated non syndromic retina degeneration.

16 Claims, 6 Drawing Sheets

Specification includes a Sequence Listing.

(56) References Cited

OTHER PUBLICATIONS

Vache et al, "Usher syndrome type 2 caused by activation of an USH2A pseudo exon: implications for diagnosis and therapy," Human Mutation, 2011, 33(1):104-108.

Zhong et al, "Generation of three-dimensional retinal tissue with functional photoreceptor from human iPSCs," Nat. Comm., 2014, 5:4047, 14 pages.

FIG. 1 uaaauauauuuuaucuuuagGGCUUAGGUGUGAUCAUUGCAAUUUGGAUUAAAUUCUCCGAAGCUUUAAUGAUGUUGGAUGUGAGCC
                    UAAAAUAGAAAUCCCGAAUCCAC-5' (Ex13-1)                  UAAAUUCUCCGAAGCUUUAAUGAUGUGAGCC
                         AAAUCCCGAAUCCACACUAGU-5' (Ex13-2)
                                                      CUAAAUUUAAAGAGGCUUCGA-5' (Ex13-3)
                                                           (Ex13-4) UACUACAACCUACACUCGG-5'

CUGCCAGUGUAACCUCCAUGGCUCAGUGAACAAAUUCUGCAAUCCUCACUCUGGGCAGUGAGUGCAAAAAGAAGCCAAGGACUUCA...
GACGGUCACAUUGGAGGUACCGAG-5' (AON1)
                                                       GAGUGAGACCCGUCACACU-5' (Ex13-5)

(...)

...GGGACCAUUUGUGACCCAAUCAGUGGCCAGUGCCUGUGUGCCUAAUCGUCAAGGAAGAAGGUAAUCAGUGUCAACCAGuaagaaa
         UUAGUCACCGGUCACGGACACA-5' (AON2)

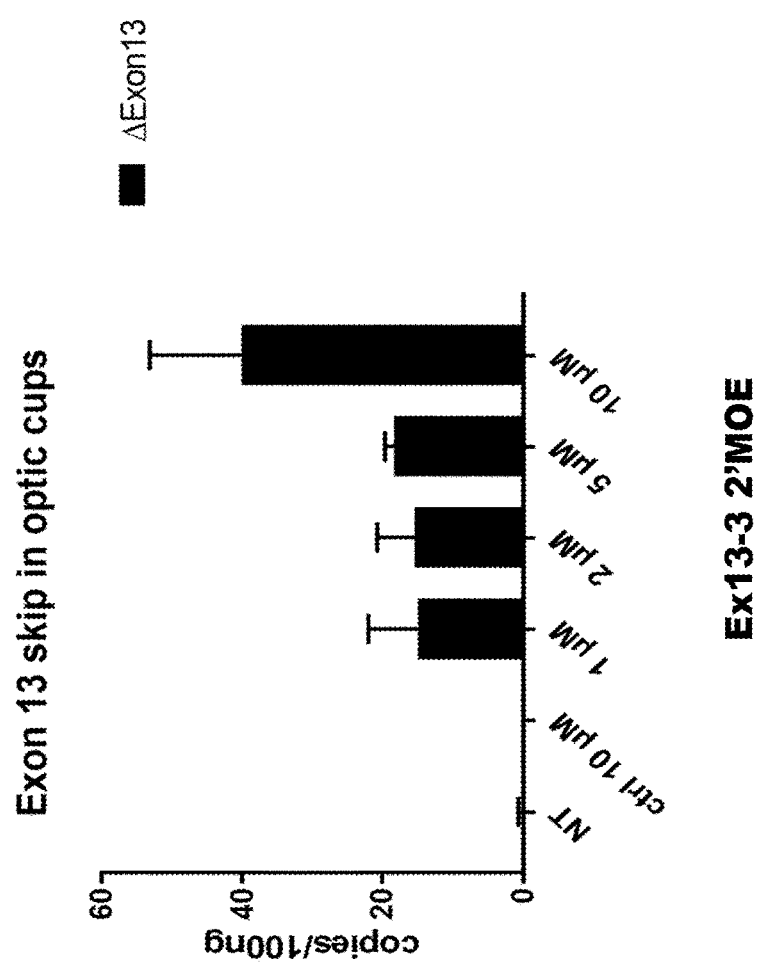

SEQUENCE LISTING

```
<160> NUMBER OF SEQ ID NOS: 23

<210> SEQ ID NO 1
<211> LENGTH: 670
<212> TYPE: DNA
<213> ORGANISM: Homo sapiens

<400> SEQUENCE: 1
taaatatatt ttatctttag ggcttaggtg tgatcattgc aattttggat ttaaatttct      60
ccgaagcttt aatgatgttg gatgtgagcc ctgccagtgt aacctccatg gctcagtgaa     120
caaattctgc aatcctcact ctgggcagtg tgagtgcaaa aaagaagcca aaggacttca     180
gtgtgacacc tgcagagaaa acttttatgg gttagatgtc accaattgta aggcctgtga     240
ctgtgacaca gctggatccc tccctgggac tgtctgtaat gctaagacag ggcagtgcat     300
ctgcaagccc aatgttgaag ggagacagtg caataaaatgt ttggagggaa acttctacct     360
acggcaaaat aattctttcc tctgtctgcc ttgcaactgt gataagactg ggacaataaa     420
tggctctctg ctgtgtaaca aatcaacagg acaatgtcct tgcaaattag gggtaacagg     480
tcttcgctgt aatcagtgtg agcctcacag gtacaatttg accattgaca attttcaaca     540
ctgccagatg tgtgagtgtg attccttggg gacattacct gggaccattt gtgacccaat     600
cagtggccag tgcctgtgtg tgcctaatcg tcaaggaaga aggtgtaatc agtgtcaacc     660
aggtaagaaa                                                           670

<210> SEQ ID NO 2
<211> LENGTH: 642
<212> TYPE: DNA
<213> ORGANISM: Homo sapiens
```

```
<400> SEQUENCE: 2
ggcttaggtg tgatcattgc aattttggat ttaaatttct ccgaagcttt aatgatgttg      60
gatgtgagcc ctgccagtgt aacctccatg gctcagtgaa caaattctgc aatcctcact     120
ctgggcagtg tgagtgcaaa aaagaagcca aaggacttca gtgtgacacc tgcagagaaa     180
acttttatgg gttagatgtc accaattgta aggcctgtga ctgtgacaca gctggatccc     240
tccctgggac tgtctgtaat gctaagacag ggcagtgcat ctgcaagccc aatgttgaag     300
ggagacagtg caataaatgt ttggagggaa acttctacct acggcaaaat aattctttcc     360
tctgtctgcc ttgcaactgt gataagactg ggacaataaa tggctctctg ctgtgtaaca     420
aatcaacagg acaatgtcct tgcaaattag gggtaacagg tcttcgctgt aatcagtgtg     480
agcctcacag gtacaatttg accattgaca attttcaaca ctgccagatg tgtgagtgtg     540
attccttggg gacattacct gggaccattt gtgacccaat cagtggccag tgcctgtgtg     600
tgcctaatcg tcaaggaaga aggtgtaatc agtgtcaacc ag                        642

<210> SEQ ID NO 3
<211> LENGTH: 24
<212> TYPE: RNA
<213> ORGANISM: Artificial Sequence
<220> FEATURE:
<223> OTHER INFORMATION: Synthetic antisense oligonucleotide AON1

<400> SEQUENCE: 3
gagccaugga gguuacacug gcag                                             24

<210> SEQ ID NO 4
<211> LENGTH: 22
<212> TYPE: RNA
<213> ORGANISM: Artificial sequence
<220> FEATURE:
<223> OTHER INFORMATION: Synthetic antisense oligonucleotide AON2

<400> SEQUENCE: 4
acacaggcac uggccacuga uu                                               22

<210> SEQ ID NO 5
<211> LENGTH: 23
<212> TYPE: DNA
<213> ORGANISM: Artificial sequence
<220> FEATURE:
<223> OTHER INFORMATION: Synthetic antisense oligonucleotide Ex13-1

<400> SEQUENCE: 5
caccuaagcc cuaaagauaa aau                                              23

<210> SEQ ID NO 6
<211> LENGTH: 21
<212> TYPE: DNA
<213> ORGANISM: Artificial sequence
<220> FEATURE:
<223> OTHER INFORMATION: Synthetic antisense oligonucleotide Ex13-2

<400> SEQUENCE: 6
ugaucacacc uaagcccuaa a                                                21

<210> SEQ ID NO 7
<211> LENGTH: 21
<212> TYPE: DNA
<213> ORGANISM: Artificial sequence
<220> FEATURE:
<223> OTHER INFORMATION: Synthetic antisense oligonucleotide Ex13-3
```

```
<400> SEQUENCE: 7
agcuucggag aaauuuaaau c                                         21

<210> SEQ ID NO 8
<211> LENGTH: 19
<212> TYPE: DNA
<213> ORGANISM: Artificial sequence
<220> FEATURE:
<223> OTHER INFORMATION: Synthetic antisense oligonucleotide Ex13-4

<400> SEQUENCE: 8
ggcucacauc caacaucau                                            19

<210> SEQ ID NO 9
<211> LENGTH: 19
<212> TYPE: DNA
<213> ORGANISM: Artificial sequence
<220> FEATURE:
<223> OTHER INFORMATION: Synthetic antisense oligonucleotide Ex13-5

<400> SEQUENCE: 9
ucacacugcc cagagugag                                            19

<210> SEQ ID NO 10
<211> LENGTH: 20
<212> TYPE: DNA
<213> ORGANISM: Artificial sequence
<220> FEATURE:
<223> OTHER INFORMATION: Synthetic primer exon 11

<400> SEQUENCE: 10
aagttggtgc agatccttcg                                           20

<210> SEQ ID NO 11
<211> LENGTH: 20
<212> TYPE: DNA
<213> ORGANISM: Artificial sequence
<220> FEATURE:
<223> OTHER INFORMATION: Synthetic primer exon 15

<400> SEQUENCE: 11
agaaacactg gcctgtgacc                                           20

<210> SEQ ID NO 12
<211> LENGTH: 23
<212> TYPE: RNA
<213> ORGANISM: Homo sapiens

<400> SEQUENCE: 12
auuuuaucuu uagggcuuag gug                                       23

<210> SEQ ID NO 13
<211> LENGTH: 21
<212> TYPE: RNA
<213> ORGANISM: Homo sapiens

<400> SEQUENCE: 13
uuuagggcuu aggugugauc a                                         21

<210> SEQ ID NO 14
<211> LENGTH: 21
<212> TYPE: RNA
<213> ORGANISM: Homo sapiens
```

-continued

```
<400> SEQUENCE: 14
gauuuaaauu ucuccgaagc u                                               21

<210> SEQ ID NO 15
<211> LENGTH: 19
<212> TYPE: RNA
<213> ORGANISM: Homo sapiens

<400> SEQUENCE: 15
augauguugg augugagcc                                                  19

<210> SEQ ID NO 16
<211> LENGTH: 19
<212> TYPE: RNA
<213> ORGANISM: Homo sapiens

<400> SEQUENCE: 16
cucacucugg gcaguguga                                                  19

<210> SEQ ID NO 17
<211> LENGTH: 20
<212> TYPE: DNA
<213> ORGANISM: Artificial sequence
<220> FEATURE:
<223> OTHER INFORMATION: Forward primer ddPCR

<400> SEQUENCE: 17
tgggacagtg gatggagata                                                 20

<210> SEQ ID NO 18
<211> LENGTH: 20
<212> TYPE: DNA
<213> ORGANISM: Artificial sequence
<220> FEATURE:
<223> OTHER INFORMATION: Reverse primer ddPCR

<400> SEQUENCE: 18
tggcattgcc tggagaaata                                                 20

<210> SEQ ID NO 19
<211> LENGTH: 24
<212> TYPE: DNA
<213> ORGANISM: Artificial sequence
<220> FEATURE:
<223> OTHER INFORMATION: Probe ddPCR

<400> SEQUENCE: 19
attcaggcca gtgcaagtgc aaag                                            24

<210> SEQ ID NO 20
<211> LENGTH: 670
<212> TYPE: RNA
<213> ORGANISM: Homo sapiens

<400> SEQUENCE: 20
uaaauauauu uuaucuuuag ggcuuaggug ugaucauugc aauuuuggau uuaaauuucu     60
ccgaagcuuu aaugauguug gaugugagcc cugccagugu aaccuccaug gcucagugaa    120
caaauucugc aauccucacu cugggcagug ugagugcaaa aaagaagcca aaggacuuca    180
gugugacacc ugcagagaaa acuuuuaugg guuagaugug accaauugua aggccuguga    240 cuguugacaca gcuggauccc ucccugggac ugucuguaau gcuaagacag ggcagugcau    300
cugcaagccc aauguugaag ggagacagug caauaaaugu uuggagggaa acuucuaccu    360
```

```
acggcaaaau aauucuuucc ucugucugcc uugcaacugu gauaagacug ggacaauaaa        420
uggcucucug cuguguaaca aaucaacagg acaauguccu ugcaaauuag ggguaacagg        480
ucuucgcugu aaucagugug agccucacag guacaauuug accauugaca auuuucaaca        540
cugccagaug ugugagugug auuccuuggg gacauuaccu gggaccauuu gugacccaau        600
caguggccag ugccugugug ugccuaaucg ucaaggaaga agguguaauc agugucaacc        660
agguaagaaa                                                              670

<210> SEQ ID NO 21
<211> LENGTH: 642
<212> TYPE: RNA
<213> ORGANISM: Homo sapiens

<400> SEQUENCE: 21
ggcuuaggug ugaucauugc aauuuuggau uuaaauuucu ccgaagcuuu aaugauguug         60
gaugugagcc cugccagugu aaccuccaug gcucagugaa caaauucugc aauccucacu        120
cugggcagug ugagugcaaa aaagaagcca aaggacuuca gugugacacc ugcagagaaa        180
acuuuuaugg guuagauguc accaauugua aggccuguga cugugacaca gcuggauccc        240
ucccugggac ugucuguaau gcuaagacag ggcagugcau cugcaagccc aauguugaag        300
ggagacagug caauaaaugu uuggagggaa acuucuaccu acggcaaaau aauucuuucc        360
ucugucugcc uugcaacugu gauaagacug ggacaauaaa uggcucucug cuguguaaca        420
aaucaacagg acaauguccu ugcaaauuag ggguaacagg ucuucgcugu aaucagugug        480
agccucacag guacaauuug accauugaca auuuucaaca cugccagaug ugugagugug        540
auuccuuggg gacauuaccu gggaccauuu gugacccaau caguggccag ugccugugug        600
ugccuaaucg ucaaggaaga agguguaauc agugucaacc ag                          642

<210> SEQ ID NO 22
<211> LENGTH: 17
<212> TYPE: RNA
<213> ORGANISM: Artificial sequence
<220> FEATURE:
<223> OTHER INFORMATION: Control AON

<400> SEQUENCE: 22
ggauagguau gagauac                                                       17

<210> SEQ ID NO 23
<211> LENGTH: 18
<212> TYPE: RNA
<213> ORGANISM: Artificial sequence
<220> FEATURE:
<223> OTHER INFORMATION: Control AON

<400> SEQUENCE: 23
ccucuuaccu caguuaca                                                      18
```

ANTISENSE OLIGONUCLEOTIDES FOR THE TREATMENT OF EYE DISEASE

CROSS-REFERENCE TO RELATED APPLICATIONS

This application is a continuation of U.S. application Ser. No. 16/336,069, filed on Mar. 22, 2019, which is a U.S. National Stage Application under 35 U.S.C. § 371 and claims the benefit of International Patent Application No. PCT/EP2017/074133, filed on Sep. 22, 2017, which claims the benefit of priority to GB Patent Application No. 1616202.6, filed on Sep. 23, 2016; the disclosures of the foregoing are incorporated herein by reference in their entirety.

SEQUENCE LISTING

This application contains a Sequence Listing that has been submitted electronically as an ASCII text file named 'SequenceListing.txt', created on Feb. 6, 2020, and is 7782 bytes in size. The material in said ASCII text file is hereby incorporated by reference in its entirety.

FIELD OF THE INVENTION

The invention relates to the fields of medicine and immunology. In particular, it relates to single-stranded antisense oligonucleotides (AONs) for use in the treatment, prevention and/or delay of eye diseases, preferably Usher syndrome type II and/or USH2A-associated retinal degeneration.

BACKGROUND OF THE INVENTION

Usher syndrome (USH, or just 'Usher') and non-syndromic retinitis pigmentosa (NSRP) are degenerative diseases of the retina. Usher is clinically and genetically heterogeneous and by far the most common type of inherited deaf-blindness in man (1 in 6,000 individuals; Kimberling et al. 2010. Frequency of Usher syndrome in two pediatric populations: implications for genetic screening of deaf and hard of hearing children. *Genet Med* 12:512-516). The hearing impairment in Usher patients is mostly stable and congenital and can be partly compensated by hearing aids or cochlear implants. NSRP is more prevalent than Usher, occurring in 1 per 4,000 individuals (Hartong et al. 2006. Retinitis pigmentosa. *Lancet* 368(9549):1795-1809). The degeneration of photoreceptor cells in Usher and NSRP is progressive and often leads to complete blindness between the third and fourth decade of life, thereby leaving time for therapeutic intervention.

Mutations in the USH2A gene are the most frequent cause of Usher explaining up to 50% of all Usher patients worldwide (±1300 patients in the Netherlands) and, as indicated by McGee et al. (2010. Novel mutations in the long isoform of the USH2A gene in patients with Usher syndrome type II or non-syndromic retinitis pigmentosa. *J Med Genet* 47(7): 499-506), also the most prevalent cause of NSRP in the USA, likely accounting for 12-25% of all cases of retinitis pigmentosa (±600 patients in the Netherlands). The mutations are spread throughout the 72 USH2A exons and their flanking intronic sequences, and consist of nonsense and missense mutations, deletions, duplications, large rearrangements, and splicing variants. Exon 13 is by far the most frequently mutated exon including two founder mutations (c.2299delG (p.E767SfsX21) in USH2 patients and c.2276G>T (p.C759F) in NSRP patients). For exon 50, fifteen pathogenic mutations have been reported, of which at least eight are clearly protein truncating. Recently the first deep-intronic mutation in intron 40 of USH2A (c.7595-2144A>G) was reported (Vache et al. 2012. Usher syndrome type 2 caused by activation of an USH2A pseudo exon: implications for diagnosis and therapy. *Human Mutation* 33(1):104-108). This mutation creates a cryptic high-quality splice donor site in intron 40 resulting in the inclusion of an aberrant exon of 152 bp (pseudo exon 40 or PE40) in the mutant USH2A mRNA, and causes premature termination of translation.

The c.2299delG mutation found in exon 13 results in a frameshift causing a premature termination codon and is presumed to lead to nonsense mediated decay. Lenassi et al. (2014. The effect of the common c.2299delG mutation in USH2A on RNA splicing. *Exp Eye Res* 122:9-12) showed that in Usher patients the mutation leads to exon 12+exon 13 double-skipping during splicing, whereas in some patients a combination was found between exon 13 only-skip, and exon12/exon 13 double-skipping. It is not uncommon for exonic sequence alterations to cause aberrant splicing. Bioinformatics tools have predicted the c.2299delG change to disrupt an exonic splicing enhancer and to create an exonic splicing silencer within exon 13. Sequence analysis has shown that skipping only aberrant exon 13, carrying the mutation, results in removal of the frameshift mutation but also results in an in-frame link between exon 12 and exon 14. Double-skipping of exon 12 and exon 13 results in an out of frame deletion when exon 11 is linked to exon 14. Hence, whereas skipping exon 13 is desired (when carrying the c.2299delG mutation) it is preferred that exon 12 is retained.

Usher and other retinal dystrophies have for long been considered as incurable disorders. Several phase I/II clinical trials using gene augmentation therapy have led to promising results in selected groups of LCA/RP/USH patients with mutations in the RPE65 (Bainbridge et al. 2008. Effect of gene therapy on visual function in Leber's congenital amaurosis. *N Engl J Med* 358, 2231-2239) and MYO7A (Hashimoto et al. 2007. Lentiviral gene replacement therapy of retinas in a mouse model for Usher syndrome type 1B. *Gene Ther* 14(7):584-594) genes. Unfortunately, the size of the coding sequence (15,606 bp) and alternative splicing of the USH2A gene and mRNA, respectively hamper gene augmentation therapy due to the currently limiting cargo size of many available vectors (such as adeno-associated virus (AAV) and lentiviral vectors).

Despite the broad clinical potential of antisense oligonucleotide (AON)-based therapy, it is not frequently used in the vertebrate eye. AONs are generally small polynucleotide molecules (16- to 25-mers) that are able to interfere with splicing as their sequence is complementary to that of target pre-mRNA molecules. The envisioned mechanism is such that upon binding of an AON to a target sequence, with which it is complementary, the targeted region within the pre-mRNA is no longer available for splicing factors which in turn results in skipping of the targeted exon. Therapeutically, this methodology can be used in two ways: a) to redirect normal splicing of genes in which mutations activate cryptic splice sites and b) to skip exons that carry mutations in such a way, that the reading frame of the mRNA remains intact and a (partially) functional protein is made. Both methods are already successfully applied in patients with severe genetic disorders (Scaffidi and Misteli. 2005. Reversal of the cellular phenotype in the premature aging disease Hutchinson-Gilford progeria syndrome. *Nat. Med* 11(4):440-445; Cirak et al. 2011. Restoration of the Dystrophin-associated Glycoprotein Complex after Exon Skipping Therapy in Duchenne Muscular Dystrophy. *Mol Ther* 20:462-467; Cirak et al. 2011. Exon skipping and dystrophin restoration in patients with Duchenne muscular dystrophy after systemic phosphorodiamidate morpholino oligomer treatment: an open-label, phase 2, dose-escalation study. Lancet 378(9791):595-605; Goemans et al. 2011. Systemic administration of PRO051 in Duchenne's muscular dystrophy. *N Engl J Med* 364(16):1513-1522). For the USH2A gene, 28 out of the 72 described exons can potentially be skipped without disturbing the overall reading frame of the transcript, including the skip of exon 13 (while exon 12 is retained).

WO 2016/005514 discloses exon skipping AONs for the USH2A pre-mRNA, directed at skipping of exon 13, exon 50 and PE40, and/or retaining exon 12. As disclosed therein, several AONs can be used for skipping exon 13. It is therefore an objective of the invention to provide alternative and more efficient AONs that can be used in a convenient therapeutic strategy for the prevention, treatment or delay of Usher and/or NSRP caused by mutations in exon 13 of the human USH2A gene.

SUMMARY OF THE INVENTION

The present invention relates to an antisense oligonucleotide (AON) for skipping exon 13 in human USH2A pre-mRNA, wherein the AON under physiological conditions binds to and/or is complementary to the sequence of SEQ ID NO: 12, 13, or 14, or a part thereof. The AON of the present invention has a positive effect on exon 13 skipping while it yields lower amounts of product in which the exon 12 and 13 are co-skipped (double skipped) as compared to known AONs that showed relatively high levels of exon 12/13 double skipping. Preferably, the AON of the present invention comprises or consists of the sequence of SEQ ID NO: 5, 6, or 7.

The present invention further relates to a pharmaceutical composition comprising an AON according to the invention, further comprising a pharmaceutically acceptable carrier. The invention also relates to an AON according to the invention, a pharmaceutical composition according to the invention, or a viral vector according to the invention, for use as a medicament, preferably for treatment, prevention or delay of a USH2A-related disease or a condition requiring modulating splicing of USH2A pre-mRNA, such as Usher syndrome type II. In yet another embodiment, the invention relates to a method for the treatment of a USH2A related disease or condition requiring modulating splicing of USH2A pre-mRNA of an individual in need thereof, said method comprising contacting a cell of said individual with an AON according to the invention, a pharmaceutical composition according to the invention, or a viral vector according to the invention.

BRIEF DESCRIPTION OF THE DRAWINGS

FIG. 1 shows part of the RNA sequence of exon 13 plus its flanking sequences (in bold; direction is 5' to 3'). Upstream and downstream intron sequences are in lower case; the exon 13 coding sequence is in upper case. The DNA sequence of exon 13 with its flanking sequences as shown here is provided as SEQ ID NO: 1, whereas the corresponding pre-mRNA sequence is provided as SEQ ID NO: 20. The coding sequence of exon 13 without flanking sequences is provided as SEQ ID NO: 2, whereas the corresponding mRNA sequence is provided as SEQ ID NO: 21. Shown here are also the sequences of the AONs described herein and their position in relation to the target RNA sequence. AON1 (SEQ ID NO: 3) and AON2 (SEQ ID NO: 4), both shown from 3' to 5' here, are known from WO 2016/005514. Ex13-1 (SEQ ID NO: 5), Ex13-2 (SEQ ID NO: 6), Ex13-3 (SEQ ID NO: 7), Ex13-4 (SEQ ID NO: 8) and Ex13-5 (SEQ ID NO: 9), also here shown from 3' to 5', are new AONs as disclosed herein.

FIG. 6 shows the exon 13 skipping results in optic cups generated from an USH2 patient, wherein the optic cups were treated with 4 different concentrations of Ex13-3 2'MOE oligonucleotide. Controls were optic cups that were not treated (NT) or that were treated with control oligonucleotide (ctrl) with an unrelated sequence but that also carried a 2'-O-methoxyethyl modification on each sugar moiety.

DETAILED DESCRIPTION

Figure 2:
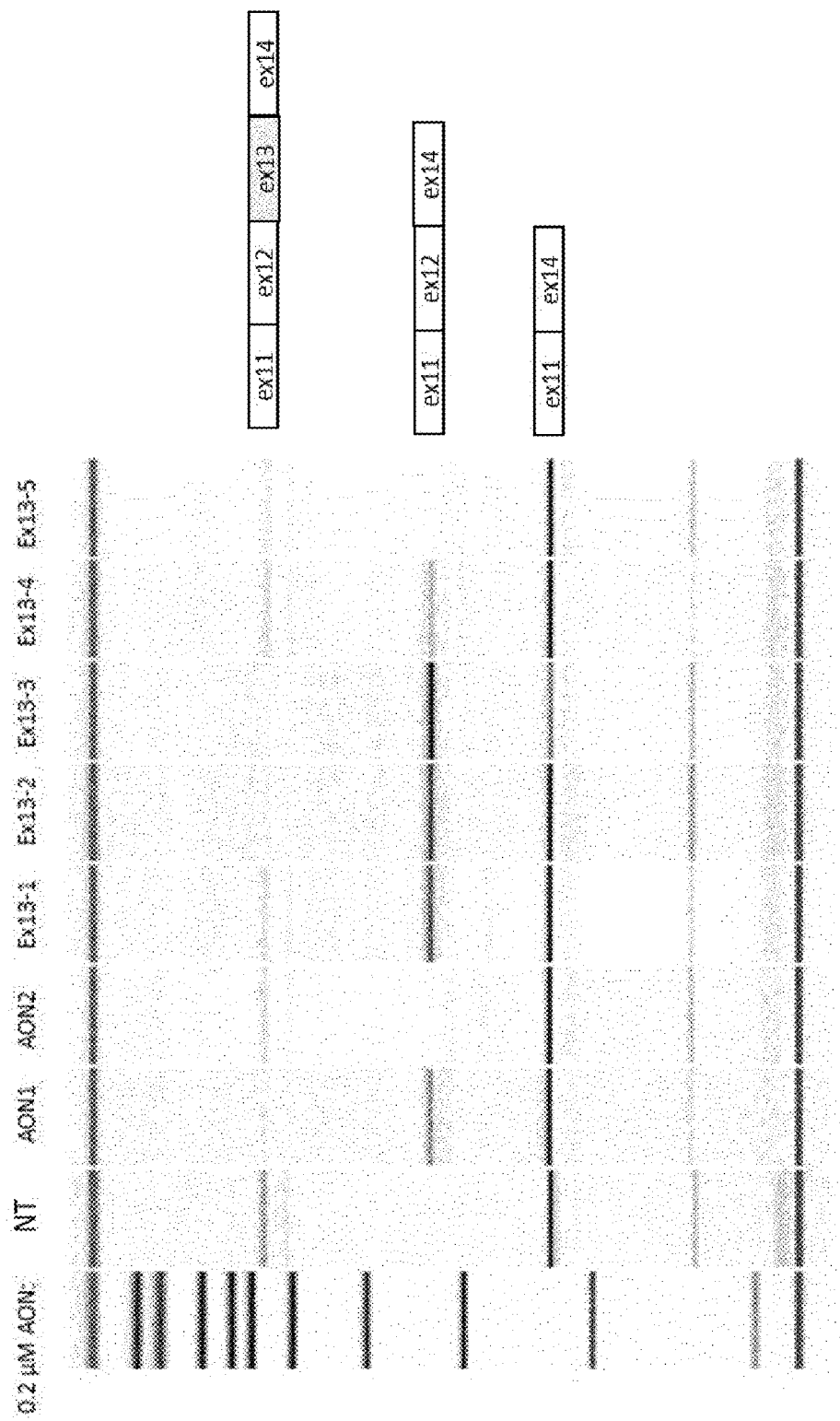
FIG. 2 shows the exon skipping results using AON1, AON2, and Ex13-1 to 5 after transfection in Weri-Rb1 cells. NT means not transfected. RT-PCR products are shown on the right, wherein each box represents the presence of an exon.

The present invention relates to specific antisense oligonucleotides (AONs) that are able to block the inclusion of aberrant exon 13 in the USH2A pre-mRNA. More specifically, the present invention relates to an AON for skipping exon 13 in human USH2A pre-mRNA, wherein the AON under physiological conditions binds to and/or is complementary to the sequence of SEQ ID NO: 12, 13, or 14, or a part thereof. The inventors of the present invention surprisingly found that an unwanted double skip of exon 12 and 13 (that results in an out of frame deletion) is reduced in levels as compared to exon 13 only-skips (which is in-frame) when using the single stranded AONs of the present invention were compared to known single stranded AONs disclosed in the prior art. It is an aim of the present invention to provide alternative and improved single stranded AONs that give significant exon 13 skipping while administration of the AON results in decreased exon12/13 double skipping, which in contrast was observed with AONs from the prior art. The inventors of the present invention were able to identify such AONs, as disclosed herein.

In one embodiment, the present invention relates to an AON for skipping exon 13 in human USH2A pre-mRNA, wherein the AON comprises or consists of the sequence of SEQ ID NO: 5, 6, or 7. In a preferred aspect said AON is an oligoribonucleotide. In a further preferred aspect the AON according to the invention comprises a 2'-0 alkyl modification, such as a 2'-O-methyl modified sugar. In a more preferred embodiment, all nucleotides in said AON are 2'-O-methyl modified. In another preferred aspect, the invention relates to an AON comprising a 2'-O-methoxyethyl modification. In a more preferred embodiment, all nucleotides of said AON carry a 2'-O-methoxyethyl modification. In yet another aspect the invention relates to an AON, wherein the AON comprises at least one 2'-O-methyl and at least one 2'-O-methoxyethyl modification. In another preferred embodiment, the AON according to the present invention has at least one phosphorothioate linkage. In another preferred aspect, all sequential nucleotides are interconnected by phosphorothioate linkages.

In yet another aspect, the invention relates to a pharmaceutical composition comprising an AON according to the invention, and a pharmaceutically acceptable carrier. Preferably, the pharmaceutical composition is for intravitreal administration and is dosed in an amount ranging from 0.05 mg and 5 mg of total AON per eye. More preferably, the pharmaceutical composition is for intravitreal administration and is dosed in an amount ranging from 0.1 and 1 mg of total AON per eye, such as about 0.1, 0.2, 0.3, 0.4, 0.5, 0.6, 0.7, 0.8, 0.9 or 1.0 mg of total AON per eye.

In yet another embodiment, the invention relates to a viral vector expressing an AON according to the invention. In yet another aspect, the invention relates to an AON according to the invention, a pharmaceutical composition according to the invention, or a viral vector according to the invention, for use as a medicament. In yet another embodiment, the invention relates to an AON according to the invention, a pharmaceutical composition according to the invention, or a viral vector according to the invention, for treatment, prevention or delay of a USH2A-related disease or a condition requiring modulating splicing of USH2A pre-mRNA, such as Usher syndrome type II.

The invention also relates to a use of an AON according to the invention, a pharmaceutical composition according to the invention, or a viral vector according to the invention for the preparation of a medicament. Preferably, said medicament is for treatment, prevention or delay of a USH2A-related disease or condition requiring modulating splicing of USH2A pre-mRNA, such as Usher syndrome type II. In yet another aspect, the invention relates to a use of an AON according to the invention, a pharmaceutical composition according to the invention, or a viral vector according to the invention, for the treatment, prevention or delay of a USH2A-related disease or condition requiring modulating splicing of USH2A pre-mRNA, such as Usher syndrome type II.

The present invention also relates to a method for modulating splicing of USH2A pre-mRNA in a cell, said method comprising contacting said cell with an AON according to the invention, a pharmaceutical composition according to the invention, or a viral vector according to the invention. In a preferred embodiment, the invention relates to a method for the treatment of a USH2A related disease or condition requiring modulating splicing of USH2A pre-mRNA of an individual in need thereof, said method comprising contacting a cell of said individual with an AON according to the invention, a pharmaceutical composition according to the invention, or a viral vector according to the invention.

In all embodiments of the invention, the terms 'modulating splicing' and 'exon skipping' are synonymous. In respect of USH2A, 'modulating splicing' or 'exon skipping' are to be construed as the exclusion of aberrant exon 13. In addition, there is provided for the retention of exon 12, preferably when exon 13 is skipped. For the purpose of the invention the terms 'aberrant exon 13' or 'aberrant USH2A exon 13' are considered to be synonymous, and considered to mean the presence of a mutation in exon 13 of the USH2A gene wherein the mutation causes disease.

The term 'exon skipping' is herein defined as inducing, producing or increasing production within a cell of a mature mRNA that does not contain a particular exon (in the current case exon 13 of the USH2A gene) that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as 'exon skipping molecules', as 'exon 13 skipping molecules', or as 'exon skipping AONs'. The term 'pre-mRNA' refers to a non-processed or partly processed precursor mRNA that is synthesized from a DNA template of a cell by transcription, such as in the nucleus.

The term 'exon retention' is herein defined as inducing, producing or increasing production within a cell of a mature mRNA that does retain a particular exon that should preferably be present in the mature mRNA. In the present case the exon that should remain is exon 12 of the USH2A gene. Exon retention is achieved by providing a cell expressing the pre-mRNA of said mature mRNA with an AON capable of interfering with sequences such as, for example, the intronic splice silencer sites in intron 12; such AON may also be referred to as an exon retention AON. The most preferred AON is an oligonucleotide that strongly induces exon 13 skipping (a phenomenon already observed in Usher patients), while at the same time not yielding too much co-skipping of exon 12. Exon 13 should be skipped as much as possible, while exon 12 should stay as much as possible.

The term 'antisense oligonucleotide' (AON) is understood to refer to a nucleotide sequence which is substantially complementary to a target nucleotide sequence in a pre-mRNA molecule, hnRNA (heterogenous nuclear RNA) or mRNA molecule. The degree of complementarity (or substantial complementarity) of the antisense sequence is preferably such that a molecule comprising the antisense sequence can form a stable double stranded hybrid with the target nucleotide sequence in the RNA molecule under physiological conditions. The terms 'antisense oligonucleotide', 'oligonucleotide' and 'oligo' are used interchangeably herein and are understood to refer to an oligonucleotide comprising an antisense sequence in respect of the target sequence.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

In one embodiment, an exon 13 skipping molecule as defined herein is an AON that binds and/or is complementary to a specified sequence. Binding to one of the specified target sequences, preferably in the context of the aberrant USH2A exon 13 may be assessed via techniques known to the skilled person. A preferred technique is gel mobility shift assay as described in EP1619249. In a preferred embodiment, an exon 13 skipping AON is said to bind to one of the specified sequences as soon as a binding of said molecule to a labeled target sequence is detectable in a gel mobility shift assay.

In all embodiments of the invention, an exon 13 skipping molecule is preferably an AON. Preferably, an exon 13 skipping AON according to the invention is an AON, which is complementary or substantially complementary to a nucleotide sequence as shown in SEQ ID NO: 12, 13, or 14.

The term 'substantially complementary' used in the context of the invention indicates that some mismatches in the antisense sequence are allowed as long as the functionality, i.e. inducing skipping of the aberrant USH2A exon 13 and retention of exon 12 is still acceptable. Preferably, the complementarity is from 90% to 100%. In general this allows for 1 or 2 mismatches in an AON of 20 nucleotides or 1, 2, 3 or 4 mismatches in an AON of 40 nucleotides, or 1, 2, 3, 4, 5, or 6 mismatches in an AON of 60 nucleotides, etc.

The invention provides a method for designing an exon 13 skipping AON able to induce skipping of the aberrant USH2A exon 13. First, said AON is selected to bind to and/or to be complementary to exon 13, possibly with stretches of the flanking intron sequences as shown in SEQ ID NO: 1 (for RNA see SEQ ID NO: 20). Subsequently, in a preferred method at least one of the following aspects has to be taken into account for designing, improving said exon skipping AON further: the exon skipping AON preferably does not contain a CpG or a stretch of CpG; and the exon skipping AON has acceptable RNA binding kinetics and/or thermodynamic properties. The presence of a CpG or a stretch of CpG in an AON is usually associated with an increased immunogenicity of said AON (Dorn and Kippenberger (2008) *Curr Opin Mol Ther* 10(1) 10-20). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an AON of the invention by detecting the presence of a neutralizing antibody and/or an antibody recognizing said AON using a standard immunoassay known to the skilled person. An inflammatory reaction, type I-like interferon production, IL-12 production and/or an increase in immunogenicity may be assessed by detecting the presence or an increasing amount of a neutralizing antibody or an antibody recognizing said AON using a standard immunoassay.

The invention allows designing an AON with acceptable RNA binding kinetics and/or thermodynamic properties. The RNA binding kinetics and/or thermodynamic properties are at least in part determined by the melting temperature of an AON (Tm; calculated with the oligonucleotide properties calculator (www.unc.edu/-cail/biotool/oligo/index) for single stranded RNA using the basic Tm and the nearest neighbor model), and/or the free energy of the AON-target exon complex (using RNA structure version 4.5). If a Tm is too high, the AON is expected to be less specific. An acceptable Tm and free energy depend on the sequence of the AON. Therefore, it is difficult to give preferred ranges for each of these parameters. An acceptable Tm may be ranged between 35 and 70° C. and an acceptable free energy may be ranged between 15 and 45 kcal/mol.

An AON of the invention is preferably one that is able to exhibit an acceptable level of functional activity. A functional activity of said AON is preferably to induce the skipping of the aberrant USH2A exon 13 plus the retention of exon 12 to a certain acceptable level, to provide an individual with a functional USH2A protein and/or mRNA and/or at least in part decreasing the production of an aberrant USH2A protein and/or mRNA. In a preferred embodiment, an AON is said to induce skipping of the aberrant USH2A exon 13, when the aberrant USH2A exon 13 skipping percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% as compared to a control RNA product not treated with an AON or a negative control AON. The aim of the present invention is to provide AONs that induce exon 13 skipping, while the amount of product wherein the exon 12 and 13 are co-skipped (double skip) is lowered. Hence, the AON should cause a double skip as limited as possible while inducing the exon 13 only skip. The AONs of the present invention display an increased exon 13 only skip and a lowered exon 12/13 double skip as compared with what was seen in the art until the present invention. Assays to determine exon skipping and/or exon retention are described in the examples herein and may be supplemented with techniques known to the person skilled in the art to judge whether an increased exon 13 only skip is found while a reduced exon 12/13 double skip is determined, when compared to known AONs.

Preferably, an AON, which comprises a sequence that is complementary or substantially complementary to a nucleotide sequence as shown in SEQ ID NO: 1 (or SEQ ID NO: 20 as RNA) of USH2A is such that the (substantially) complementary part is at least 50% of the length of the AON according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an AON according to the invention comprises or consists of a sequence that is complementary to part of SEQ ID NO: 2 (or in fact its RNA equivalent as shown in SEQ ID NO: 21), more preferably to SEQ ID NO: 12, 13, or 14.

In another preferred embodiment, the length of said complementary part of said AON is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding of a protein to the AON, or to modify a thermodynamic property of the AON, more preferably to modify target RNA binding affinity.

It is thus not absolutely required that all the bases in the region of complementarity are capable of pairing with bases in the opposing strand. For instance, when designing the AON one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, 'sufficiently' preferably means that using a gel mobility shift assay as described in example 1 of EP1619249, binding of an AON is detectable.

Optionally, said AON may further be tested by transfection into retina cells of patients. Skipping of targeted exon 13 and/or retention of exon 12 may be assessed by RT-PCR (such as e.g. described in EP1619249 and WO 2016/005514). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the AON also will be able to hybridize to one or more other pre-mRNA molecules decreases with increasing size of the AON. It is clear that AONs comprising mismatches in the region of complementarity but that retain the capacity to hybridize and/or bind to the targeted region(s) in the pre-mRNA, can be used in the invention. However, preferably at least the complementary parts do not comprise such mismatches as AONs lacking mismatches in the complementary part typically have a higher efficiency and a higher specificity, than AONs having such mismatches in one or more complementary regions. It is thought that higher hybridization strengths (i.e. increasing number of interactions with the opposing strand) are favorable in increasing the efficiency of the process of interfering with the splicing machinery of the system. Preferably, the complementarity is from 90% to 100%. In general this allows for 1 or 2 mismatches in an AON of 20 nucleotides or 1, 2, 3, or 4 mismatches in an AON of 40 nucleotides, or 1, 2, 3, 4, 5, or 6 mismatches in an AON of 60 nucleotides, etc.

An exon skipping AON of the invention is preferably an isolated single stranded molecule in the absence of its (target) counterpart sequence. An exon skipping AON of the invention is preferably complementary to, or under physiological conditions binds to a sequence selected from SEQ ID NO: 12, 13, or 14, and most preferably complementary to, or under physiological conditions binds to the sequence of SEQ ID NO: 14.

A preferred exon 13 skipping AON of the invention comprises or consists of from 8 to 143 nucleotides, more preferably from 10 to 40 nucleotides, more preferably from 12 to 30 nucleotides, more preferably from 20 to 30 nucleotides, and preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon 13 skipping AON selected from the group consisting of SEQ ID NO: 5, 6, or 7. In a preferred embodiment, the invention provides an exon 13 skipping AON comprising or preferably consisting of the sequence as provided in SEQ ID NO: 7. It was found that this molecule is very efficient in modulating splicing of the aberrant USH2A exon 13, while, at the same time it appeared very efficient to cause retention of exon 12 better than the AONs of the prior art. One may also say that the AON of the present invention is less efficient in causing an exon 12/13 double skip, but is very efficient in causing an "exon 13 only" skip. This preferred exon 13 skipping AON of the invention (without causing too much, or very lowered levels of exon 12/13 double skips), as provided in SEQ ID NO: 7 preferably comprises 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon 13 skipping AON according to the invention may contain one of more RNA residues, or one or more DNA residues, and/or one or more nucleotide analogues or equivalents, as will be further detailed herein below. It is preferred that an exon 13 skipping AON of the invention comprises one or more residues that are modified to increase nuclease resistance, and/or to increase the affinity of the AON for the target sequence. Therefore, in a preferred embodiment, the AON sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) *Chem Commun* 495-497). Since the backbone of a PNA molecule contains no charged phosphate groups, PNA-RNA hybrids are usually more stable than RNA-RNA or RNA-DNA hybrids, respectively (Egholm et al. (1993) *Nature* 365:566-568). A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or di-substituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylamino oxyethoxy; and -dimethylaminoethoxyethoxy. The sugar moiety can be a pyranose or derivative thereof, or a deoxypyranose or derivative thereof, preferably ribose or derivative thereof, or deoxyribose or derivative thereof. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. *Nucleic Acid Res* Supplement No. 1:241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an AON to be modified uniformly. In addition, more than one of the aforementioned analogues or equivalents may be incorporated in a single AON or even at a single position within an AON. In certain embodiments, an AON of the invention has at least two different types of analogues or equivalents. A preferred exon skipping AON according to the invention comprises a 2'-0 alkyl phosphorothioated antisense oligonucleotide, such as 2'-O-methyl modified ribose (RNA), 2'-O-ethyl modified ribose, 2'-O-propyl modified ribose, and/or substituted derivatives of these modifications such as halogenated derivatives. An effective AON according to the invention comprises a 2'-O-methyl ribose with a (preferably full) phosphorothioated backbone.

It will also be understood by a skilled person that different AONs can be combined for efficiently skipping of the aberrant USH2A exon 13. In a preferred embodiment, a combination of at least two AONs are used in a method of the invention, such as 2, 3, 4, or 5 different AONs. Hence, the invention also relates to a set of AONs comprising at least one AON according to the present invention, optionally further comprising AONs as disclosed herein or as disclosed in the prior art, such as AON4a as disclosed in WO 2016/005514 that appeared to be one of the better performers related to exon 12 retention.

As indicated in great detail above, the presence of the mutation in exon 13 induces skipping of exon 13 and co-skipping of exon 12. The art has shown that using an AON that causes skipping of exon 13 is (to a certain level) accompanied by exon 12 skipping, which is unwanted. Hence, it is preferred to use an AON that yields efficient exon 13 skipping while retaining exon 12. It is most preferred that a single AON provides proper exon 13 skipping on the one hand and retention of exon 12 on the other. As can be seen in FIG. 2, use of the AONs of the prior art give a significant higher level of exon 12/13 double skip than exon 13 single skip (see intensity of the bands). It is preferred to use an AON that at least gives as much exon 13 single skip in comparison to an exon 12/13 double skip, which would be approximately 50/50. FIG. 2 shows that the AONs of the present invention were able to give at least a 50/50 ratio, whereas Ex13-3 was even more efficient in giving a single exon 13 skip over an exon 12/13 double skip. Ratios can be determined by the person skilled in the art using common quantitative PCR techniques, and the present invention provides at least one method to determine the ratio, as illustrated by the examples herein. It is held here that the AONs herein referred to as Ex13-1 (SEQ ID NO: 5), Ex13-2 (SEQ ID NO: 6), and Ex13-3 (SEQ ID NO: 7), or at least an AON that binds to and/or is complementary to SEQ ID NO: 12, 13, or 14 fulfill the requirement of having at least a 50/50 ratio (exon 13 single skip/exon 12/13 double skip). The AONs of the present invention outperform the AONs of the prior art.

An AON can be linked to a moiety that enhances uptake of the AON in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon 13 skipping AON according to the invention may be indirectly administrated using suitable means known in the art. It may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an AON as identified herein. Accordingly, the invention provides a viral vector expressing an exon 13 skipping AON according to the invention when placed under conditions conducive to expression of the exon skipping AON. A cell can be provided with an exon skipping molecule capable of interfering with essential sequences that result in highly efficient skipping of the aberrant USH2A exon 13 by plasmid-derived AON expression or viral expression provided by adenovirus- or adeno-associated virus-based vectors. Expression may be driven by a polymerase II-promoter (Pol II) such as a U7 promoter or a polymerase III (Pol III) promoter, such as a U6 RNA promoter. A preferred delivery vehicle is a viral vector such as an adeno associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from Pol III promoters, and/or wherein transcripts are in the form fusions with U1 or U7 transcripts, which yield good results for delivering small transcripts. It is within the skill of the artisan to design suitable transcripts. Preferred are Pol III driven transcripts, preferably, in the form of a fusion transcript with an U1 or U7 transcript. Such fusions may be generated as described (Gorman et al. 1998. Stable alteration of pre-mRNA splicing patterns by modified U7 small nuclear RNAs. *Proc Natl Acad Sci USA* 95(9):4929-34; Suter et al. 1999. Double-target antisense U7 snRNAs promote efficient skipping of an aberrant exon in three human beta-thalassemic mutations. *Hum Mol Genet* 8(13): 2415-23).

The exon 13 skipping AON may be delivered as such. However, the exon 13 skipping AON may also be encoded by the viral vector. Typically, this is in the form of an RNA transcript that comprises the sequence of an oligonucleotide according to the invention in a part of the transcript. An AAV vector according to the invention is a recombinant AAV vector and refers to an AAV vector comprising part of an AAV genome comprising an encoded exon 13 skipping AON according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention. Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector. More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector. More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector. More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector. A nucleic acid molecule encoding an exon 13 skipping AON according to the invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art. The AAV helper functions can be supplied on an AAV helper construct, which may be a plasmid.

Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand. "AAV helper virus" provides additional functions required for AAV replication and packaging.

Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference. Preferably, an AAV genome as present in a recombinant AAV vector according to the invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art. Preferably, an AAV vector according to the invention is constructed and produced according to the methods in the Examples herein. A preferred AAV vector according to the invention is an AAV vector, preferably an AAV2/5, AAV2/8, AAV2/9 or AAV2/2 vector, expressing an USH2A exon 13 skipping AON according to the invention that comprises, or preferably consists of, a sequence that is complementary or substantially complementary to a nucleotide sequence as shown in SEQ ID NO: 12, 13, or 14. A further preferred AAV vector according to the invention is an AAV vector, preferably an AAV2/5, AAV2/8, AAV2/9 or AAV2/2 vector, expressing an exon 13 skipping AON according to the invention that comprises, or preferably consists of, SEQ ID NO: 5, 6, or 7.

Improvements in means for providing an individual or a cell, tissue, organ of said individual with an exon 13 skipping AON according to the invention, are anticipated considering the progress that has already thus far been achieved. Such future improvements may of course be incorporated to achieve the mentioned effect on restructuring of mRNA using a method of the invention. An exon 13 skipping AON according to the invention can be delivered as is to an individual, a cell, tissue or organ of said individual. When administering an exon 13 skipping AON according to the invention, it is preferred that the AON is dissolved in a solution that is compatible with the delivery method. Retina or inner ear cells can be provided with a plasmid for AON expression by providing the plasmid in an aqueous solution. Alternatively, a preferred delivery method for an AON or a plasmid for AON expression is a viral vector or nanoparticles. Preferably viral vectors or nanoparticles are delivered to retina or inner ear cells. Such delivery to retina or inner ear cells or other relevant cells may be in vivo, in vitro or ex vivo. Nanoparticles and micro particles that may be used for in vivo AON delivery are well known in the art. Alternatively, a plasmid can be provided by transfection using known transfection reagents. For intravenous, subcutaneous, intramuscular, intrathecal and/or intraventricular administration it is preferred that the solution is a physiological salt solution. Particularly preferred in the invention is the use of an excipient or transfection reagents that will aid in delivery of each of the constituents as defined herein to a cell and/or into a cell (preferably a retina cell). Preferred are excipients or transfection reagents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection reagents comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each constituent as defined herein to a cell, preferably a retina cell. Such excipients have been shown to efficiently deliver an AON to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity. Lipofectin represents an example of a liposomal transfection agent. It consists of two lipid components, a cationic lipid N-[1-(2,3 dioleoyloxy)propyl]-N, N, N-trimethylammonium chloride (DOTMA) (cp. DOTAP which is the methylsulfate salt) and a neutral lipid dioleoylphosphatidyl ethanolamine (DOPE). The neutral component mediates the intracellular release. Another group of delivery systems are polymeric nanoparticles. Polycations such as diethylamino ethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver AONs across cell membranes into cells. In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an AON. The skilled person may select and adapt any of the above or other commercially available alternative excipients and delivery systems to package and deliver an exon skipping molecule for use in the current invention to deliver it for the prevention, treatment or delay of a USH2A related disease or condition. "Prevention, treatment or delay of a USH2A related disease or condition" is herein preferably defined as preventing, halting, ceasing the progression of, or reversing partial or complete visual impairment or blindness, as well as preventing, halting, ceasing the progression of or reversing partial or complete auditory impairment or deafness that is caused by a genetic defect in the USH2A gene.

In addition, an exon 13 skipping AON according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes. Therefore, in a preferred embodiment, an exon 13 skipping AON according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon 13 skipping AON according to the invention and a further adjunct compound as later defined herein. If required, an exon 13 skipping AON according to the invention or a vector, preferably a viral vector, expressing an exon 13 skipping AON according to the invention can be incorporated into a pharmaceutically active mixture by adding a pharmaceutically acceptable carrier. Accordingly, the invention also provides a composition, preferably a pharmaceutical composition, comprising an exon 13 skipping AON according to the invention, or a viral vector according to the invention and a pharmaceutically acceptable excipient. Such composition may comprise a single exon 13 skipping AON or viral vector according to the invention, but may also comprise multiple, distinct exon 13 skipping AON or viral vectors according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington (Remington. 2000. The Science and Practice of Pharmacy, 20th Edition. Baltimore, Md.: Lippincott Williams Wilkins). Each feature of said composition has earlier been defined herein.

A preferred route of administration is through intra-vitreal injection of an aqueous solution or specially adapted formulation for intraocular administration. EP2425814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

If multiple distinct exon 13 skipping AONs according to the invention are used, concentration or dose defined herein may refer to the total concentration or dose of all AONs used or the concentration or dose of each exon 13 skipping AONs used or added. Therefore in one embodiment, there is provided a composition wherein each or the total amount of exon 13 skipping AONs according to the invention used is dosed in an amount ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

A preferred USH2A exon 13 skipping AON according to the invention is for the treatment of a USH2A related disease or condition of an individual. In all embodiments of the invention, the term 'treatment' is understood to include also the prevention and/or delay of the USH2A related disease or condition. An individual, which may be treated using an exon 13 skipping AON according to the invention may already have been diagnosed as having a USH2A related disease or condition. Alternatively, an individual which may be treated using an exon 13 skipping AON according to the invention may not have yet been diagnosed as having a USH2A related disease or condition but may be an individual having an increased risk of developing a USH2A related disease or condition in the future given his or her genetic background. A preferred individual is a human individual. In a preferred embodiment the USH2A related disease or condition is Usher syndrome type II. Accordingly, the invention further provides an exon 13 skipping AON according to the invention, or a viral vector according to the invention, or a composition according to the invention for use as a medicament, for treating a USH2A related disease or condition requiring modulating splicing of USH2A and for use as a medicament for the prevention, treatment or delay of a USH2A related disease or condition. A preferred USH2A related disease or condition is Usher syndrome type II. Each feature of said use has earlier been defined herein.

The invention further provides the use of an exon 13 skipping AON according to the invention, or of a viral vector according to the invention, or a composition according to the invention for the treatment of a USH2A related disease or condition requiring modulating splicing of USH2A. In a preferred embodiment the USH2A related disease or condition is Usher syndrome type II.

The invention further provides the use of an exon 13 skipping AON according to the invention, or of a viral vector according to the invention, or a composition according to the invention for the preparation of a medicament, for the preparation of a medicament for treating a USH2A related disease or condition requiring modulating splicing of USH2A and for the preparation of a medicament for the prevention, treatment or delay of a USH2A related disease or condition. A preferred USH2A related disease or condition is Usher syndrome type II. Therefore in a further aspect, there is provided the use of an exon 13 skipping AON, viral vector or composition as defined herein for the preparation of a medicament, for the preparation of a medicament for treating a condition requiring modulating splicing of USH2A and for the preparation of a medicament for the prevention, treatment or delay of a USH2A related disease or condition. A preferred USH2A related disease or condition is Usher syndrome type II. Each feature of said use has earlier been defined herein.

A treatment in a use or in a method according to the invention is at least once, lasts one week, one month, several months, 1, 2, 3, 4, 5, 6 years or longer, such as lifelong. Each exon 13 skipping AON or equivalent thereof as defined herein for use according to the invention may be suitable for direct administration to a cell, tissue and/or an organ in vivo of individuals already affected or at risk of developing USH2A related disease or condition, and may be administered directly in vivo, ex vivo or in vitro. The frequency of administration of an AON, composition, compound or adjunct compound of the invention may depend on several parameters such as the severity of the disease, the age of the patient, the mutation of the patient, the number of exon 13 skipping AONs (i.e. dose), the formulation of said AON, the route of administration and so forth. The frequency may vary between daily, weekly, at least once in two weeks, or three weeks or four weeks or five weeks or a longer time period. Dose ranges of an exon 13 skipping AON according to the invention are preferably designed on the basis of rising dose studies in clinical trials (in vivo use) for which rigorous protocol requirements exist. An exon 13 skipping AON as defined herein, may be used at a dose which is ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg. In a preferred embodiment, a concentration of an AON as defined herein, which is ranged from 0.1 nM and 1 µM is used. Preferably, this range is for in vitro use in a cellular model such as retinal cells or retinal tissue. More preferably, the concentration used is ranged from 1 to 400 nM, even more preferably from 10 to 200 nM, even more preferably from 50 to 100 nM. If several AONs are used, this concentration or dose may refer to the total concentration or dose of AONs or the concentration or dose of each AON added. In a preferred embodiment, a viral vector, preferably an AAV vector as described earlier herein, as delivery vehicle for a molecule according to the invention, is administered in a dose ranging from $1\times10^9$ to $1\times10^{17}$ virus particles per injection, more preferably from $1\times10^{10}$ to $1\times10^{12}$ virus particles per injection. The ranges of concentration or dose of AONs as given above are preferred concentrations or doses for in vivo, in vitro or ex vivo uses. The skilled person will understand that depending on the AONs used, the target cell to be treated, the gene target and its expression levels, the medium used and the transfection and incubation conditions, the concentration or dose of AONs used may further vary and may need to be optimized any further.

An exon 13 skipping AON according to the invention, or a viral vector according to the invention, or a composition according to the invention for use according to the invention may be suitable for administration to a cell, tissue and/or an organ in vivo of individuals already affected or at risk of developing a USH2A related disease or condition, and may be administered in vivo, ex vivo or in vitro. Said exon 13 skipping AON according to the invention, or viral vector according to the invention, or composition according to the invention may be directly or indirectly administered to a cell, tissue and/or an organ in vivo of an individual already affected by or at risk of developing a USH2A related disease or condition, and may be administered directly or indirectly in vivo, ex vivo or in vitro. As Usher syndrome type II has a pronounced phenotype in retina and inner ear cells, it is preferred that said cells are retina or inner ear cells, it is further preferred that said tissue is the retina or the inner ear and/or it is further preferred that said organ is the eye or the ear.

The invention further provides a method for modulating splicing of USH2A in a cell comprising contacting the cell, preferably a retina cell, with an exon 13 skipping AON according to the invention, or a viral vector according to the invention, or a composition according to the invention. The features of this aspect are preferably those defined earlier herein. Contacting the cell with an exon 13 skipping AON according to the invention, or a viral vector according to the invention, or a composition according to the invention may be performed by any method known by the person skilled in the art. Use of the methods for delivery of exon 13 skipping AONs, viral vectors and compositions described herein is included. Contacting may be directly or indirectly and may be in vivo, ex vivo or in vitro.

The invention further provides a method for the treatment of a USH2A related disease or condition requiring modulating splicing of USH2A of an individual in need thereof, said method comprising contacting a cell, preferably a retina cell, of said individual with an exon 13 skipping AON according to the invention, or a viral vector according to the invention, or a composition according to the invention. The features of this aspect are preferably those defined earlier herein. Contacting the cell, preferably a retina cell with an exon 13 skipping AON according to the invention, or a viral vector according to the invention, or a composition according to the invention may be performed by any method known by the person skilled in the art. Use of the methods for delivery of AONs, viral vectors and compositions described herein is included. Contacting may be directly or indirectly and may be in vivo, ex vivo or in vitro. Unless otherwise indicated each embodiment as described herein may be combined with another embodiment as described herein.

The sequence information as provided herein should not be so narrowly construed as to require inclusion of erroneously identified bases. The skilled person is capable of identifying such erroneously identified bases and knows how to correct for such errors. All patent and literature references cited in the present specification are hereby incorporated by reference in their entirety.

EXAMPLES

Example 1. Providing and Testing Alternative Antisense Oligonucleotides (AONs) for Efficient Skipping of Exon 13 in Human USH2A Pre-mRNA The sequence of exon 13 of the human USH2A gene further analyzed for the presence of exonic splice enhancer motifs. Multiple sites were initially determined (see FIG. 1) and subsequently five RNA AONs (Ex13-1 to Ex13-5) were purchased from IDT, and designed with a Tm of 58° C. Initially all AONs were modified with a 2'-O-methyl group at the sugar chain and all had a full phosphorothioated backbone. AONs were kept dissolved in phosphate buffered saline.

Culture conditions, transfection, RT-PCR and analysis protocols were as described in WO 2016/005514, and using general methods known to the person skilled in the art. Human retinoblastoma cells (Weri-Rb1) were cultured in RPMI1640 medium (Gibco) containing 10% (v/v) fetal calf serum (Sigma), 1% 10 U/µl penicillin, 10 µg/µl streptomycin (Gibco) and 1% GlutaMAX (Gibco), at a density of $0.5 \times 10^6$ cells/ml. Cells were passaged twice a week.

AON1, AON2 and Ex13-1 to Ex13-5 antisense oligonucleotides were tested first for their ability to skip exon 13 from the USH2A pre-mRNA. Prior to transfection, $1.0 \times 10^6$ Weri-Rb1 cells were seeded in each well of a 6-wells plate, in a total volume of 0.9 ml Optimem. Transfection mixtures were prepared by combining 50 µl Optimem supplemented with 1 µl AON in a desired concentration and 50 µl Optimem supplemented with 1.25 µl Lipofectamine 2000 (Invitrogen). Both mixtures were incubated for 5 min at RT. After this incubation step both mixtures were mixed together thoroughly and incubated for another 20 min at RT, before addition to the cells. 48 hours after transfection, cells were collected and washed with 1×PBS, before directly proceeding to RNA isolation. Total RNA was isolated from transfected cells using the Nucleospin RNA II isolation kit (Machery Nagel) according to manufacturer's protocol. Subsequently, 1 µg of total RNA was used for cDNA synthesis using the iScript cDNA synthesis kit (Bio-Rad). 5% of the cDNA was used for each PCR reaction. Part of the USH2A cDNA was amplified under standard PCR conditions using a forward primer (provided herein as SEQ ID NO: 10) and a reverse primer (provided herein as SEQ ID NO: 11) that are located in exon 11 and exon 15 of the human USH2A gene, respectively. PCR products were resolved on a 1.5% agarose gel. Bands presumably representing correctly and aberrantly spliced USH2A were excised from the gel, purified using Nucleospin Extract II isolation kit and sequenced from both strands for confirmation with the ABIPRISM Big Dye Terminator Cycle Sequencing V2.0 Ready Reaction kit and the ABIPRISM 3730 DNA analyzer (Applied Biosystems).

Figure 5:
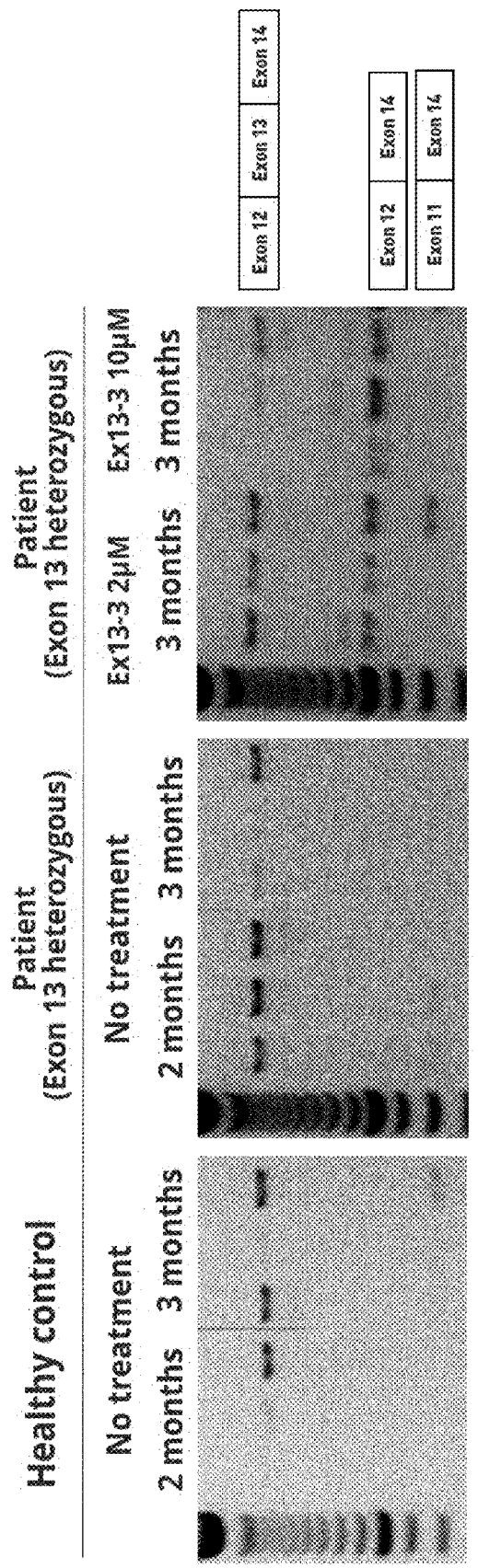
FIG. 5 shows the exon skipping results in optic cups, treated with Ex13-3 oligonucleotide that was fully 2'-O-methyl modified and contained a full phosphorothioated backbone. Controls were optic cups generated from fibroblasts from a healthy donor and optic cups from USH2A patient fibroblasts that received no treatment with AONs. The six separate lanes in the left and middle panel represent results from untreated optic cups (in triplo) differentiated for 2 or 3 months, as indicated, and the three separate lanes per concentration AON in the right panel represent results from treated optic cups (in triplo) differentiated for 3 months and that were incubated with two different concentrations Ex13-3 AONs for 1 month.

RT-PCR analysis revealed the expression of USH2A mRNA in Weri-Rb1 cells and that transfection of AON1 resulted in skipping of only exon 13 as well as in double skipping of exon 12/13 (FIG. 5 in WO 2016/005514). The aim of the new AONs as disclosed herein was to see whether oligonucleotides could be identified that more efficiently left exon 12 in, with an increase of the exon 13 only skip product. Using a forward primer located in exon 11 and a reverse primer in exon 15 the RT products were analyzed and revealed that such was indeed possible. FIG. 2 shows the results using AON1 and AON2 as controls and Ex13-1 to Ex13-5 as the newly identified AONs. It is clear that AON2 predominantly induces a double skip of exon 12 and exon 13, with hardly any signal of the exon 13 only skip. Surprisingly, Ex13-1, Ex13-2 and Ex13-3 appeared to give a stronger signal for the single (exon 13) skip than AON1 and Ex13-4, whereas that signal was almost absent in the case of Ex13-5. The non-spliced product (higher up in the gel) appeared almost absent after transfection with Ex13-3. Also, the signal of the double exon 12/13 skip after using Ex13-3 was lower in intensity than the single (exon 13) skip, indicating a strong improvement over the known AONs.

Example 2. Exon 13 Skipping in Weri-Rb1 Cells Using AONs with Different Chemical Modifications Culture conditions, transfection, RT-PCR and analysis protocols were as described in WO 2016/005514 and as in example 1 above. 1.0×10⁶ Weri-Rb1 cells were seeded in each well of a 6-wells plate prior to incubation. Cells were incubated gymnotically (hence, without transfection reagents) with a synthetic and isolated oligonucleotide with the Ex13-3 sequence (SEQ ID NO: 7) but carrying 5 different kinds of chemical modification patterns (purchased from LGD Biosearch):
Ex13-3 2'OMe (or Ex13-3 OMe)=2'-O-methyl modification in all sugar entities indicated by 'm' (lower case) and full phosphorothioated backbone indicated by an asterisk (*):
5'-mA*mG*mC*mU*mU*mC*mG*mG*mA*mG*mA* mA*mA*mU*mU*mU*mA*mA*mA*mU*mC-3'
Ex13-3 2'MOE (or Ex13-3 MOE)=2'-O-methoxyethyl modification in all sugar entities indicated by 'M' (upper case) and full phosphorothioated backbone indicated by an asterisk (*); all 2'-O-methoxyethyl modified U's are in fact 5-methyluridine (=m⁵U or thymidine) and all 2'-O-methoxyethyl modified C's are in fact 5-methylcytosine (m⁵C):
5'-MA*MG*MC*MU*MU*MC*MG*MG*MA*MG* MA*MA*MA*MU*MU*MU*MA*MA*MA*MU*MC-3'
Ex13-3 MOE OMe=2'-O-methoxyethyl modifications or 2'-O-methyl modifications in sugar entities indicated by 'M' (upper case) and 'm' (lower case) respectively, and full phosphorothioated backbone indicated by an asterisk (*); all 2'-O-methoxyethyl modified U's are in fact 5-methyluridine (=m⁵U or thymidine) and all 2'-O-methoxyethyl modified C's are in fact 5-methylcytosine (m⁵C):
5'-MA*MG*MC*MU*MU*mC*mG*mG*mA*mG* mA*mA*mA*mU*mU*mU*MA*MA*MA*MU*MC-3'
Ex13-3 8PS=2'-O-methyl modification in all sugar entities indicated by 'm' (lower case) and 8 phosphorothioate linkages in the backbone (4 on each terminus) indicated by an asterisk (*):
5'-mA*mG*mC*mU*mUmCmGmGmAmGmAmAm AmUmUmUmA*mA*mA*mU*mC-3'
Ex13-3 11PS=2'-O-methyl modification in all sugar entities indicated by 'm' (lower case) and 11 phosphorothiate linkages distributed over the backbone indicated by an asterisk (*):
5'-mA*mG*mC*mUmU*mCmG*mGmAmGmAmA* mAmU*mUmU*mAmA*mA*mU*mC-3'

Figure 3:
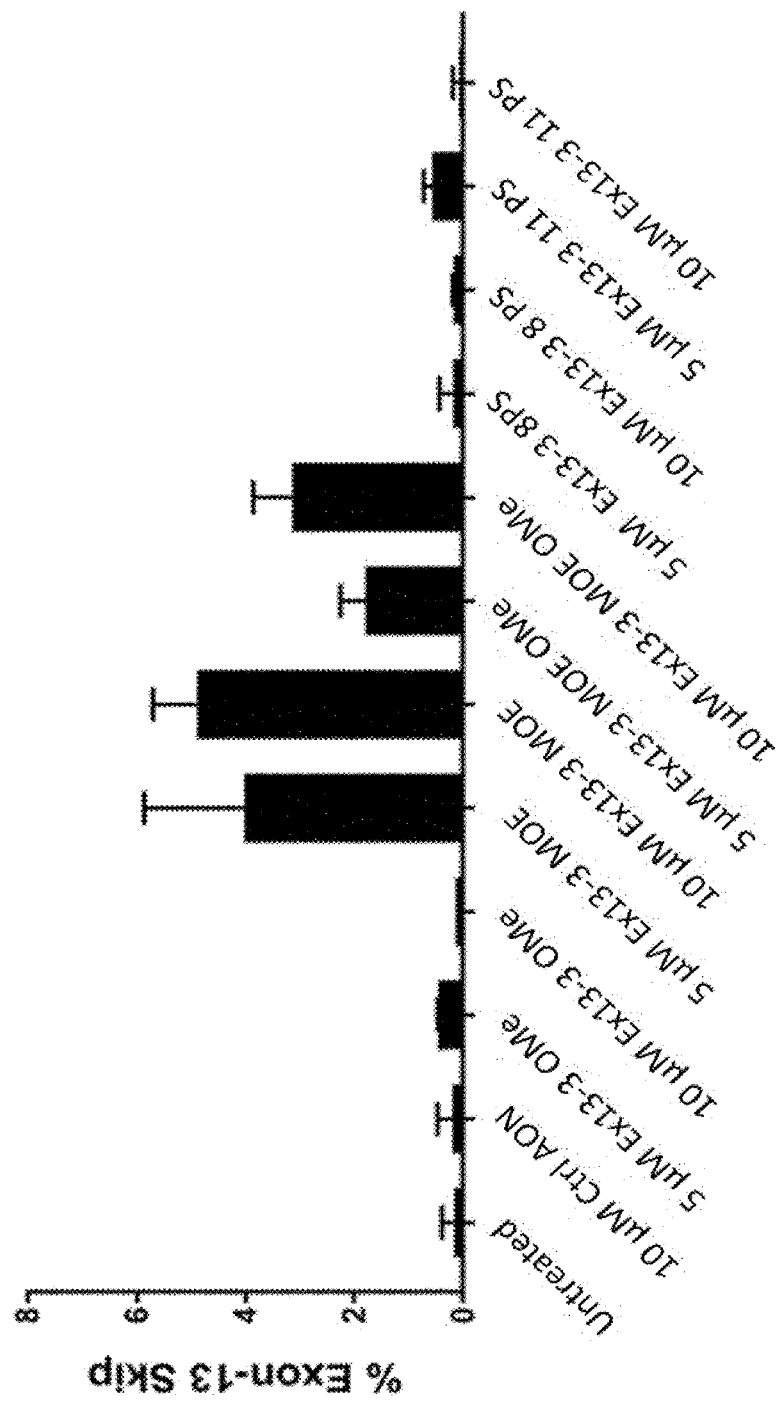
FIG. 3 shows the ddPCR results on RNA obtained from Weri-Rb1 cells that were gymnotically treated (no transfection reagents) with five different Ex13-3 oligonucleotides carrying five different chemical modifications to the sugar moiety. The percentage of exon 13 skipped mRNA (in a wild type non-skipped background) is depicted.

The AONs were incubated with the cells for 48 h in two different concentrations: 5 and 10 µM. The control AON contained a full phosphorothioated backbone and contained a 2'-O-methyl modification on each sugar moiety. The control AON had the following sequence: 5'-GGAUAG-GUAUGAGAUAC-3' (SEQ ID NO: 22) and was used in a concentration of 10 µM. After incubation, cells were collected and washed with 1×PBS, before directly proceeding to RNA isolation. Total RNA was isolated as described in example 1. A multiplex droplet digital PCR (ddPCR) reaction was performed with two Taqman gene expression assays to quantify total USH2A expression (Applied Biosystems, #Hs01071797_m1) and an assay to quantify the percentage exon 13 skip in USH2A (Applied Biosystems, #Hs01071800_m1) mRNAs. A forward primer (provided herein as SEQ ID NO: 17), a reverse primer (provided herein as SEQ ID NO: 18) and a 6-fluorescein amidite (6-FAM) labeled probe (herein provided as SEQ ID NO: 19) that are located in exon 13 and 14 of the human USH2A gene were used to determine the exon 13 skip in USH2A mRNA. The manufacturer's protocol was used to prepare ddPCR mixes using supermix for probes (no dUTP; Bio-Rad, #186-3025). The ddPCR assay was performed on a QX2000 Droplet Digital PCR system (Bio-Rad). Analysis was performed with Quanta Life Software (Bio-Rad) and Microsoft Excel. Total USH2A mRNA levels were used to correct for wild-type and exon 13 skipped USH2A mRNA levels. FIG. 3 shows the results obtained with Ex13-3 oligonucleotide carrying the different chemical modifications as outlined above. It is clearly visible that-under these conditions where no transfection reagents were used—the 2'-O-methoxyethyl (2'-O-MOE; or 2'-MOE=2'-methoxyethoxy) modification used alone or in combination with the 2'-O-methyl (2'-OMe) modification is superior to the 2'-OMe modification alone, or to the 8PS or 11 PS modifications. Hence, an AON according to the present invention preferably carries at least one nucleotide with a 2'-O-MOE modification in the sugar moiety or is fully 2'-O-MOE modified. Under these gymnotic conditions as much as 5% exon skipping was achieved.

Figure 4:
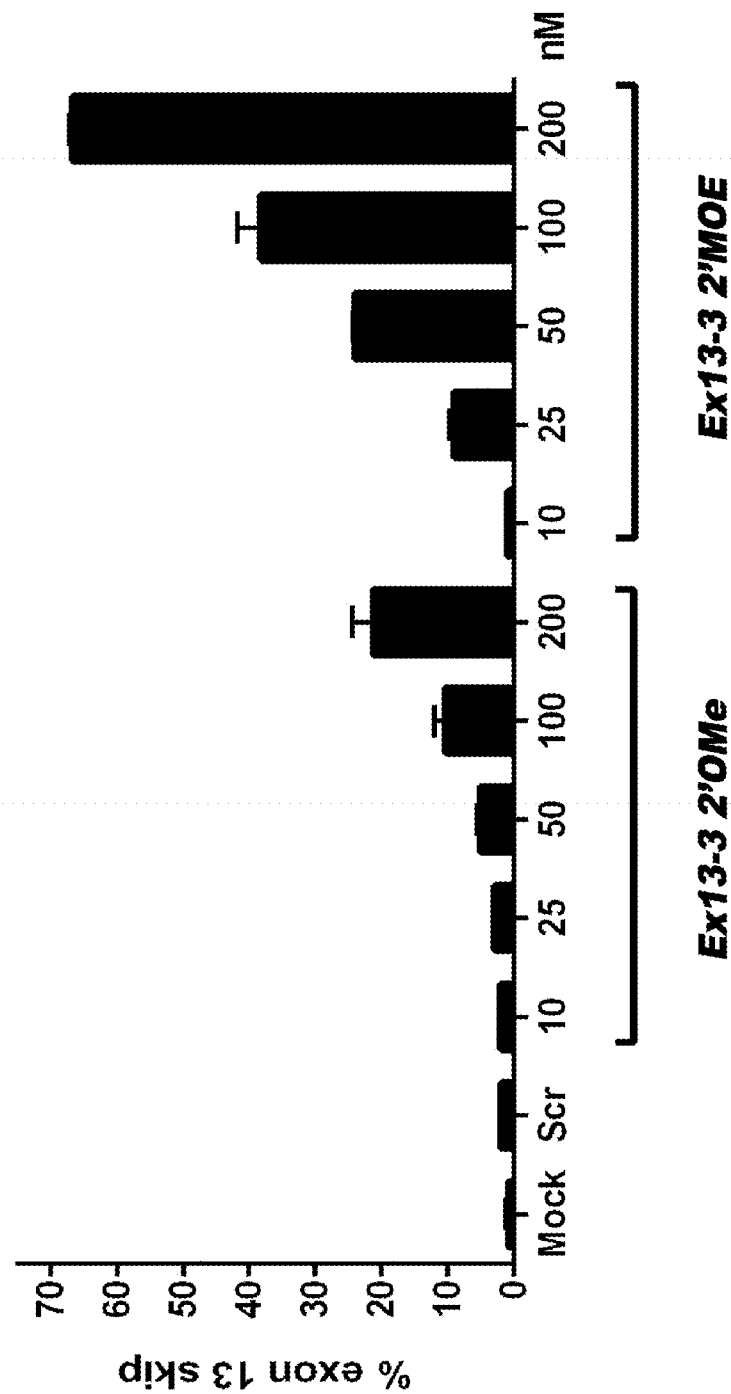
FIG. 4 shows the ddPCR results on RNA obtained from Weri-Rb1 cells transfected with different concentrations of Ex13-3 oligonucleotides that were either fully modified with 2'-O-methyl on the sugar entity (Ex13-3 2'OMe; left), or fully modified with 2'-O-methoxyethyl (Ex13-3 2'MOE; right) on the sugar entity.

The fully 2'-O-methyl and the fully 2'-O-methoxyethyl Ex13-3 versions were then tested in a dose-response experiment, but now with transfection reagents, again on Weri-Rb1 cells. The experiment was carried out as described in example 1, using a scrambled (Scr) version of the Ex13-3 AON as a control, and the ddPCR analysis was as described above and was again used to determine the percentage of exon 13 skipped mRNA. Concentrations of 10, 25, 50, 100 and 200 nM transfected AON were tested. The control AON was only used in the highest concentration of 200 nM. Results are shown in FIG. 4, and clearly indicate the increase in exon skipping effect when increasing concentrations of AON were used, and also clearly shows the superior effect of the 2'-O-methoxyethyl modification over the AON carrying only 2'-O-methyl modifications at the sugar moieties.

Example 3. AONs Induce Exon 13 Skipping in Optic Cups Generated from USH2A Patient Fibroblasts Fibroblasts from an USH2 patient carrying both USH2A c.7595-2144A>G (p.Lys2532Thrfs*56) and c.2299delG (p.Glu767Serfs) mutations in compound heterozygosity and fibroblasts from a healthy donor were used for optic cup generation. Fibroblasts from these individuals were reprogrammed using four lentiviruses expressing Oct3/4, Sox2, Klf4 and c-Myc by the Radboud UMC Stem Cell Technology Centre (Okita et al. 2011. A more efficient method to generate integration-free human iPS cells. *Nat Methods* 8:409-412). In brief, induced pluripotent stem cell (iPSC) lines were generated on feeder cells (mouse embryonic fibroblasts), and subsequently maintained in Essential 8 medium (Life Technologies; cat #A1517001). Three clones were cryopreserved at passage ~6 and further analysed for expression of the pluripotent stem cell markers: SSEA-4, NANOG, TRA1-81 and OCT3/4 by immunocytochemistry. In addition, qPCR analysis was performed for pluripotency markers LIN28, NANOG, OCT3/4 and SOX2 after total RNA isolation as described in example 1. Then, iPSC colonies were picked and cultured in suspension with mTeSR1 medium to induce aggregate formation. Aggregates were gradually transitioned into neural-induction medium. After seven days aggregates were seeded onto Matrigel-coated dished and the medium was changed daily. In the fourth week of differentiation, horseshoe-shaped NR domains were manually detached with a sharpened Tungsten needle and cultured in suspension for 2 or 3 months where they gradually formed 3-dimensional optic cups (for details see Zhong et al. 2014. Generation of three-dimensional retinal tissue with functional photoreceptor from human iPSCs. *Nat Comm* 5:4047).

After successful generation of the iPSC-derived optic cups (after 3 months differentiation) these were treated with an Ex13-3 oligonucleotide that was fully 2'-O-methyl modified and contained a full phosphorothioated backbone. Treatment lasted 1 month with two different concentrations: 2 µM and 10 µM, which was performed by refreshing the medium containing the AON every other day. USH2A transcript analysis was performed to determine wild-type versus exon 13-skipped levels in the mature mRNA with primers located in the flanking exons 11 and 15. FIG. 5 shows the results of these analyses (optic cups were generated in triplo and each lane represents one optic cup). Non-treated optic cups revealed a wild-type band of 1239 bp. Treatment of optic cups with either 2 µM or 10 µM Ex13-3 resulted in a band without exon 13 of 597 bp. Occasionally a band of 401 bp (representing double-skipping of exon 12 and exon 13) occurred in both the optic cups from the healthy donor as well as the patient-derived optic cups.

In a subsequent experiment, optic cups were generated from fibroblasts of an USH2 patient having the USH2A c.2299delG (p.Glu767Serfs) mutation in homozygosity, as described above, with the exception that iPSC colonies were picked and cultured to form embryoid bodies (as described in Sangermano et al. 2016. *Ophthalmology* 123(6):1375-85). In brief, embryoid bodies were gradually transitioned into differentiation medium. After seven days embryoid bodies were seeded onto Matrigel-coated dishes and the medium was changed daily to form optic cups.

After successful generation the optic cups were then treated with the Ex13-3 2'MOE antisense oligonucleotide (see Example 2) for 1 month using 1 µM, 2 µM, 5 µM and 10 µM concentration by refreshing the medium containing the AON every other day. As a control, an AON was used that had a fully phosphorothioated backbone and that also did carry a 2'-O-methoxyethyl modification on each sugar moiety, with the following sequence: 5'-CCUCUUAC-CUCAGUUACA-3' (SEQ ID NO: 23). In this control AON, all 2'-O-methoxyethyl modified U's are in fact 5-methyluridine (=$m^5U$ or thymidine) and all 2'-O-methoxyethyl modified C's are in fact 5-methylcytosine (m5C).

USH2A transcript analysis was then used to determine wild-type versus exon-13 skipped levels in the mRNA. A multiplex ddPCR reaction was performed as described in Example 2. Total USH2A mRNA levels were used to correct for wildtype and exon 13 USH2A mRNA levels. FIG. 6 shows the ddPCR results obtained with the Ex13-3 2'MOE oligonucleotide on optic cups. It is clearly visible that— under these gymnotic conditions where no transfection reagents were used—the 2'-O-methoxyethyl modification used alone is effective in inducing an exon 13 skip in the USH2A mRNA. Hence, an AON according to the present invention preferably carries at least one nucleotide with a 2'-O-MOE modification in the sugar moiety or, in another preferred embodiment, is fully 2'-O-MOE modified.

These data convincingly show that treatment with an exon skipping inducing AON, without using transfection reagents, on an in vitro eye model, results in significant skipping of exon 13 in USH2A pre-mRNA in USH2A-patient material.

The invention claimed is:

1. An antisense oligonucleotide (AON) that under physiological conditions binds to and/or is complementary to the sequence of SEQ ID NO: 12, 13, or 14, or a part thereof, wherein at least one nucleotide of the antisense oligonucleotide comprises a sugar moiety that is mono- or di-substituted at the 2', 3' and/or 5' position.

2. The AON according to claim 1, wherein the AON is an oligoribonucleotide.

3. The AON according to claim 1, wherein the substituent at the 2', 3' and/or 5' position is selected from the group consisting of:
 —OH;
 —F;
 substituted or unsubstituted, linear or branched lower (C1-C10) alkyl, alkenyl, alkynyl, alkaryl, allyl, or aralkyl, that may be interrupted by one or more heteroatoms;
 O-alkyl, S-alkyl, or N-alkyl;
 O-alkenyl, S-alkenyl, or N-alkenyl;

O-alkynyl, S-alkynyl, or N-alkynyl;
O-allyl, S-allyl, of N-allyl;
O-alkyl-O-alkyl;
methoxy;
aminopropoxy;
methoxyethoxy;
dimethylamino oxyethoxy; and
dimethylaminoethoxyethoxy.

4. The AON according to claim 1, wherein the at least one nucleotide comprises a 2'-Omethyl modified sugar and/or a 2'-O-methoxyethyl modified sugar.

5. The AON according to claim 4, wherein all nucleotides in the AON are 2'-O-methyl modified or wherein all nucleotides are 2'-O-methoxyethyl modified.

6. The AON according to claim 4, wherein the AON is an oligoribonucleotide comprising a 2'-O-methyl and a 2'-O-methoxyethyl modification.

7. The AON according to claim 1, wherein the AON has at least one phosphorothioate linkage.

8. The AON according to claim 7, wherein all sequential nucleotides are interconnected by phosphorothioate linkages.

9. A pharmaceutical composition comprising an AON according to claim 1 and a pharmaceutically acceptable carrier.

10. The pharmaceutical composition according to claim 9, wherein the pharmaceutical composition is for intravitreal administration and is adapted for a dosage in an amount ranging from 0.05 mg and 5 mg of total AON per eye.

11. An in vitro method for modulating splicing of USH2A pre-mRNA in a cell, the method comprising contacting the cell with an AON according to claim 1.

12. An in vitro method for modulating splicing of USH2A pre-mRNA in a cell, the method comprising contacting the cell with a pharmaceutical composition according to claim 9.

13. A method for the treatment of a USH2A related disease or condition requiring modulating splicing of USH2A pre-mRNA in an individual in need thereof, the method comprising administering a therapeutically effective amount of the AON according to claim 1.

14. A method for the treatment of a USH2A related disease or condition requiring modulating splicing of USH2A pre-mRNA in an individual in need thereof, the method comprising administering a therapeutically effective amount of the pharmaceutical composition according to claim 9.

15. The method according to claim 13, wherein the USH2A-related disease or condition requiring modulating splicing of USH2A pre-mRNA is Usher syndrome type II or non-syndromic retinitis pigmentosa.

16. The method according to claim 14, wherein the USH2A-related disease or condition requiring modulating splicing of USH2A pre-mRNA is Usher syndrome type II or non-syndromic retinitis pigmentosa.

* * * * *

UNITED STATES PATENT AND TRADEMARK OFFICE
CERTIFICATE OF CORRECTION

PATENT NO. : 11,479,771 B2
APPLICATION NO. : 16/784410
DATED : October 25, 2022
INVENTOR(S) : Hester Catharina Van Diepen, Janne Juha Turunen and Hee Lam Chan It is certified that error appears in the above-identified patent and that said Letters Patent is hereby corrected as shown below:

On the Title Page

Column 2, Line 36, item (56) under "OTHER PUBLICATIONS", delete "affnity" and insert
-- affinity --

Column 2, Line 38, item (56) under "OTHER PUBLICATIONS", delete "ofDNA" and insert
-- of DNA --

Column 2, Line 43, item (56) under "OTHER PUBLICATIONS", delete "International International" and insert -- International --

Column 2, Line 55, item (56) under "OTHER PUBLICATIONS", delete "thalassemic" and insert
-- thalassemia --

In the Claims

Column 33, Line 10 (approx.), Claim 4, delete "2'-Omethyl" and insert -- 2'-O-methyl --

Signed and Sealed this
Twenty-fourth Day of January, 2023

Katherine Kelly Vidal
*Director of the United States Patent and Trademark Office*